United States Patent [19]

Deluca et al.

[11] Patent Number: 5,597,815
[45] Date of Patent: Jan. 28, 1997

[54] PREVENTION OF HYPERPHOSPHATEMIA IN KIDNEY DISORDER PATIENTS

[75] Inventors: Hector F. Deluca, Deerfield, Wis.; Eduardo Slatopolsky, St. Louis, Mo.

[73] Assignee: Wisconsin Alumni Research Foundation, Madison, Wis.

[21] Appl. No.: 502,288

[22] Filed: Jul. 13, 1995

[51] Int. Cl.[6] ................................................ A61K 31/59
[52] U.S. Cl. ................................................ 514/167
[58] Field of Search ................................................ 514/167

[56] References Cited

U.S. PATENT DOCUMENTS

| | | | |
|---|---|---|---|
| 5,063,221 | 11/1991 | Nishii et al. | 514/167 |
| 5,086,191 | 8/1992 | Deluca et al. | 552/653 |
| 5,237,110 | 8/1993 | Deluca et al. | 568/665 |
| 5,246,925 | 9/1993 | Deluca et al. | 514/167 |
| 5,281,731 | 1/1994 | Deluca et al. | 552/653 |

OTHER PUBLICATIONS

Lee et al., Abstract Proc. Workshop Vitam. D (1979).

*Primary Examiner*—Phyllis G. Spivack
*Attorney, Agent, or Firm*—Andrus, Sceales, Starke & Sawall

[57] ABSTRACT

The 19-nor-vitamin D analogs, and particularly 19-nor-1α,25-dihydroxyvitamin $D_2$, possess low calcemic and phosphatemic activity while also having the ability to suppress parathyroid hormone (PTH) production. The suppressive effect on PTH secretion of these 19-nor analogs without significant changes in serum calcium or serum phosphorus make them ideal tools for the treatment of secondary hyperparathyroidism in patients having kidney disorders.

11 Claims, 5 Drawing Sheets

PREVENTION OF HYPERPHOSPHATEMIA IN KIDNEY DISORDER PATIENTS

This invention was made with U.S. Government support awarded by the National Institutes of Health (NIH) Grant No. DK-14881. The U.S. Government has certain rights in this invention.

BACKGROUND OF THE INVENTION

Vitamin D is essential for life in higher animals. It is one of the important regulators of calcium and phosphorus and is required for proper development and maintenance of bone. However, during the past decade, the spectrum of activities promoted by 1,25-$(OH)_2D_3$ has been found to extend far beyond a role in calcium homeostasis. In addition to its action on the intestine, bone, kidney, and parathyroid glands to control serum calcium, this hormone has been shown to have important cell differentiating activity. Receptors for this hormone have been identified in dozens of different target cells that respond to 1,25-$(OH)_2D_3$ with a diverse range of biological action. These newly discovered activities have suggested other therapeutic applications of 1,25-$(OH)_2D_3$ including hyperparathyroidism, psoriasis, cancer, and immune regulation.

Secondary hyperparathyroidism is a universal complication in patients with chronic renal failure. Because of its ability to suppress parathyroid hormone (PTH), 1,25-$(OH)_2D_3$ has been used with success in the treatment of secondary hyperparathyroidism, Slatopolsy, et al, "Marked Suppression of Secondary Hyperparathyroidism by Intravenous Administration of 1,25-dihydroxycholecalciferol in Uremic Patients", J. Clin. Invest. 74:2136–2143, 1984. Its use is often precluded, however, by the development of hypercalcemia resulting from its potent action on intestinal absorption and bone mineral mobilization.

Hyperphosphatemia is also a persistent problem in chronic hemodialysis patients and can be further aggravated by therapeutic doses of 1,25-$(OH)_2D_3$. Delmez et al, "Hyperphosphatemia: Its Consequences and Treatment in Patients with Chronic Renal Disease", Am. J. Kidney Dis. 19:303–317, 1992; Quarles et al, "Prospective Trial of Pulse Oral versus Intravenous Calcitriol Treatment of Hyperparathyroidism in ESRD", Kidney Int. 45:1710–1721,1994. In addition, the control of phosphate absorption with large doses of calcium carbonate, Meyrier et al, "The Influence of a High Calcium Carbonate Intake on Bone Disease in Patients Undergoing Hemodialysis", Kidney Int. 4:146–153, 1973; Moriniere et al, "Substitution of Aluminum Hydroxide by High Doses of Calcium Carbonate in Patients on Chronic Hemodialysis: Disappearance of Hyperaluminaemia and Equal Control of Hyperparathyroidism", Proc. Eur. Dial Transplant Assoc. 19: 784–787, 1983; Slatopolsky et al, "Calcium Carbonate as a Phosphate Binder in Patients with Chronic Renal Failure Undergoing Dialysis", New Engl. J. Med. 315:157–161, 1986, only increases the risk of hypercalcemia from 1,25-$(OH)_2D_3$ therapy. Thus, an analog of 1,25-$(OH)_2D_3$ that can suppress PTH with minor effects on calcium and phosphate metabolism would be an ideal tool for the control of secondary hyperparathyroidism.

SUMMARY OF THE INVENTION

A method of preventing hyperphosphatemia in a patient having a kidney disorder comprising administering to said patient a vitamin D compound that suppresses PTH and minimizes intestinal phosphorus absorption. Preferably, the vitamin D compound is a 19-nor-vitamin D compound and most preferably is 19-nor-1α,25-dihydroxyvitamin $D_2$.

DESCRIPTION OF THE INVENTION

Figure 1:
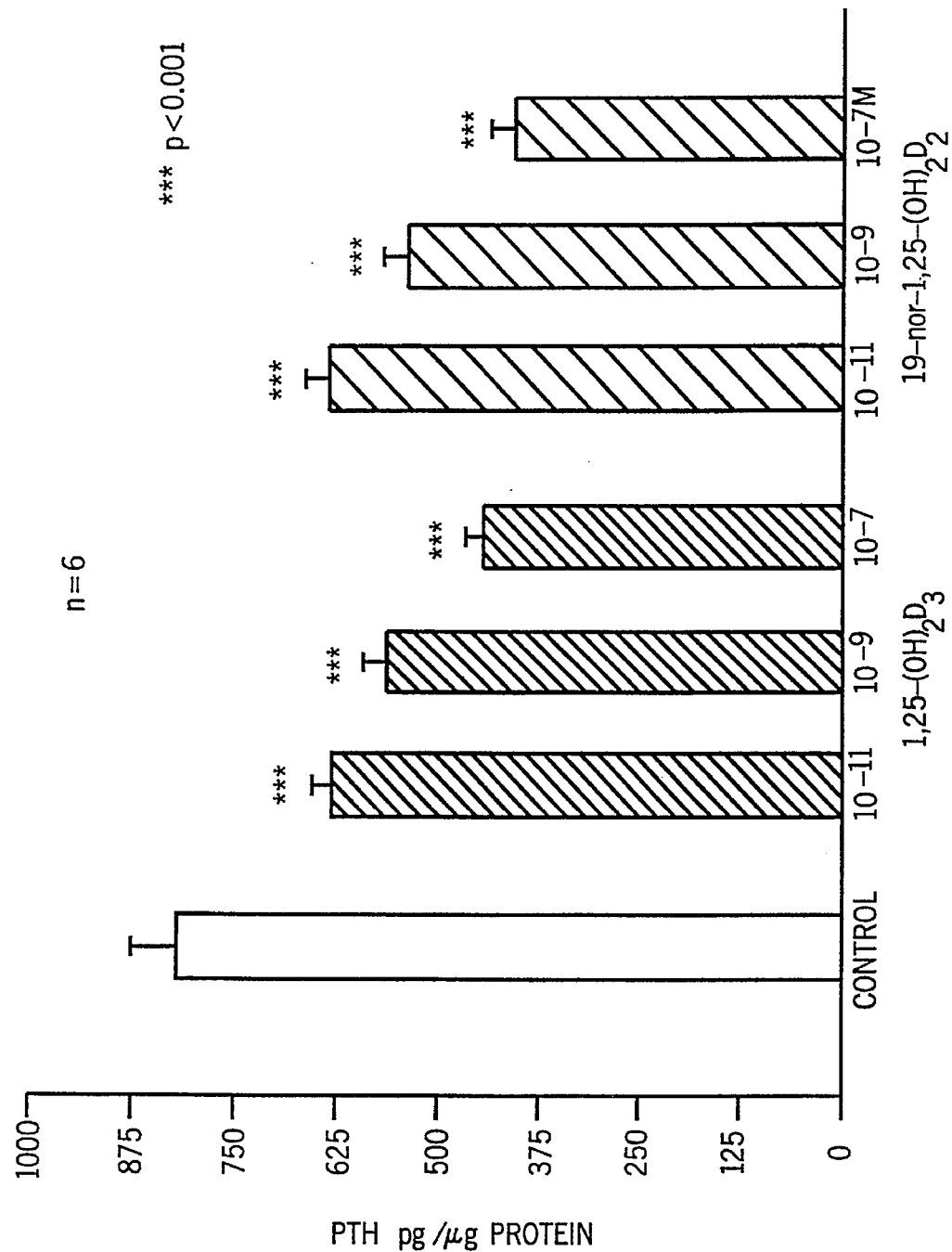
FIG. 1 illustrates the effects of 1,25-$(OH)_2D_3$ and 19-nor, 1,25-$(OH)_2D_2$ on PTH secretion in primary culture of bovine parathyroid cells.

Compounds useful in the present invention are those vitamin D compounds that can suppress PTH while at the same time having minimal or no effects on calcium and phosphate metabolism. A class of vitamin D compounds which satisfy, such criteria are the 19-nor-analogs, i.e. compounds in which the ring A exocyclic methylene group (carbon 19) typical of all vitamin D system has been removed and replaced by two hydrogen atoms. Structurally these novel analogs are characterized by the general formula I shown below:

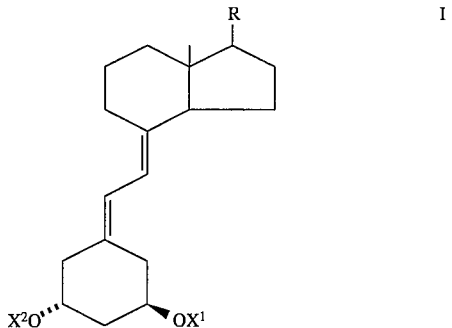

where $X^1$ and $X^2$ each represent, independently, hydrogen or a hydroxy-protecting group.

The side chain group R in the above-shown structure I may represent any of the presently known steroid side chain types. More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below:

where the stereochemical center (corresponding to C-20 in steroid numbering) may have the R or S configuration, (i.e.

either the natural configuration about carbon 20 or the 20-epi configuration), and where Z is selected from Y, —OY, —CH$_2$OY, —C≡CY and —CH=CHY, where the double bond may have the cis or trans geometry,, and where Y is selected from hydrogen, methyl, —CR$^5$O and a radical of the structure.

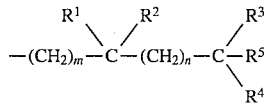

where m and n, independently, represent integers from 0 to 5, where R$^1$ is selected from hydrogen, hydroxy, protected hydroxy, fluoro, trifluoromethyl, and C$_{1-5}$— alkyl, which may be straight chain or branched and, optionally, bear a hydroxy or protected -hydroxy substituent, and where each of R$^2$, R$^3$, and R$^4$, independently, is selected from hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, where R$^5$ represents hydrogen, hydroxy, protected hydroxy, or C$_{1-5}$ alkyl, and where any of the groups at positions 20, 22 and 23, respectively in the side chain may be replaced by an oxygen atom.

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkyl or arylsilyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl," "fluoroalkyl" and "deuteroalkyl" refer to such an alkyl radical substituted by one or more hydroxy, fluoro or deuterium groups respectively. An "acyl" group is an alkanoyl group of 1 to 6 carbons in all its isomeric forms, or an aroyl group, such as benzoyl, or halo-, nitro- or alkyl-substituted benzoyl groups, or an alkoxycarbonyl group of the type Alkyl—O—CO—, such as methoxycarbonyl, ethoxycarbonyl, propyloxycarbonyl, etc., or a dicarboxylic acyl group such as oxalyl, malonyl, succinoyl, glutaroyl, or adiopoyl. The term "aryl" signifies a phenyl-, or an alkyl, nitro- or halo-substituted phenyl group. The term alkoxy signifies the group alkyl-O—.

Specific important examples of side chains are the structures represented by formulas (a), (b), (c), (d) and (e) below, i.e., the side chain as it occurs in 25-hydroxyvitamin D$_3$ (a); vitamin D$_3$ (b); 25-hydroxyvitamin D$_2$ (c); vitamin D$_2$ (d); and the C-24-epimer of 25-hydroxyvitamin D$_2$ (e).

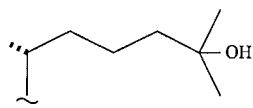

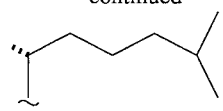

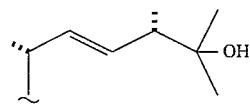

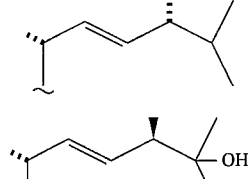

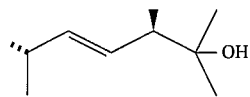

More specifically, a preferred compound for use in the present invention is 19-nor-1α,25-dihydroxyvitamin D$_2$, i.e. formula I wherein X$^1$ and X$^2$ are both hydrogen together with side chain (c) shown above.

A method of synthesis of 19-nor-vitamin D compounds has been reported by Perlman et al, Tetrahedron Letters 13, 1823 (1990). This method involves the removal of the C-19-methylene group in an existing vitamin D compound, and is also disclosed in U.S. Pat. Nos. 5,237,110 and 5,246,925. Another method involves a convergent synthesis of 19-nor-vitamin D compounds, and is disclosed in U.S. Pat. No. 5,281,731. Still another method involves the condensation of a bicyclic ketone with a phosphine oxide derivative, and is disclosed in U.S. Pat. No. 5,086,191.

For treatment purposes, the active compounds of this invention can be formulated as solutions in innocuous solvents, or as emulsions, suspensions or dispersions in suitable innocuous solvents or carriers, or as pills, tablets or capsules, containing solid carriers according to conventional methods known in the art. For topical applications the compounds are advantageously formulated as creams or ointments or similar vehicle suitable for topical applications. Any such formulations may also contain other pharmaceutically-acceptable and non-toxic excipients such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal, or topically in the form of ointments, lotions, or in suitable transdermal patches. In the treatment of hyperparathyroidism, the compounds are administered in dosages sufficient to suppress parathyroid activity, so as to achieve parathyroid hormone levels in the normal range. Suitable dosage amounts are from 1 to 500 μg of compound per day, such dosages being adjusted, depending on diseases to be treated, its severity and the response or condition of the subject as well-understood in the art.

This invention is more specifically described by the following illustrative examples.

MATERIALS AND METHODS

PTH Secretion in Culture or Bovine Parathyroid Cells

Primary monolayer cell cultures of bovine parathyroid cells were prepared according to the method of MacGregor et al with minor modifications. MacGregor et al, "Primary Monolayer Cell Culture of Bovine Parathyroids: Effects of Calcium Isoproterenol and Growth Factors", Endocrinology 30:313–328, 1983. Briefly, bovine parathyroid glands were trimmed of extraneous tissue, sliced to ⁻0.5 mm thickness with a Stadie-Riggs tissue slicer (Thomas Scientific, Swedesboro, N.J.) and placed in DME (HG)/Ham's F-12 culture medium (50/50) containing 2.5 mg/ml collagenase (Boehringer Mannheim, Indianapolis, Ind.) and 0.5 mM total calcium. The suspension (1 g tissue per 10 ml media) was agitated in a shaking water bath at 37° for 90 minutes, and periodically aspirated through a large bore hole cut in an Eppendorf pipet tip attached to a 60-ml syringe. The digested tissue was filtered through gauze, resuspended, and washed three times with culture medium containing DME (HG)/Ham's F12 medium (50/50), 1 mM total calcium, 4% newborn calf serum, 15 mM Hepes, 100 IU/ml penicillin, 100 μg/ml streptomycin, 5 μg/ml insulin, 2 mM glutamine, and 1% nonessential amino acids. Cells were plated at 80,000 cells/cm$^2$. After 24 hours, the medium was replaced with the same medium as described above, with the exception that the serum was replaced with 1 mg/ml bovine serum albumin and 5 μg/ml holotransferrin. This medium was replenished every 24 to 48 hours.

PTH Secretion Studies

The test media, containing various concentrations of 1,25-(OH)$_2$D$_3$ or 19-nor-1,25-(OH)$_2$D$_2$ were prepared by adding the indicated ethanol solutions of the compounds to the media; final ethanol concentration was 0.1%. After incubation, media were collected, centrifuged, and then stored at −20° C. until analyzed for PTH. PTH was assayed using antibody CH9, which recognizes intact, mid-region, and carboxy-terminal fragments of PTH. Details of the recognition characteristics of the antisera and the radioimmunoassay (RIA) methodology have been described previously in Hruska et al, "Metabolism of Immunoreactive Parathyroid Hormone in the Dog. The Role of the Kidney and the Effects of Chronic Renal Disease", J. Clin. Invest. 56:39–48, 1975. Cellular protein in each sample was determined by sonicating the cells into 1 mM NaOH and assaying an aliquot by using a protein assay kit (Bio-Rad Laboratories, Richmond, Calif.). All PTH values were corrected for cell protein.

Reverse Transcriptase-Polymerase Chain Reaction (RT-PCR)

The pair of parathyroid glands from a single animal was homogenized in 250 μl of RNAzol (Cinna Biotech, Houston, Tx.), mixed with 25 μl of chloroform, vortexed and centrifuged in a microfuge to separate phases. The upper aqueous phase (125 μl) was mixed with 20 μ1 of 1 mg/ml glycogen, 145 μl of 2-propanol and placed at −20° C. overnight. The coprecipitated total RNA and glycogen were gathered by centrifugation (microfuge) and washed twice with 70% ethanol. Oligo dT primed cDNA was prepared from 40% of the total RNA with the aid of a kit obtained from Promega (Madison, Wis.). One sixth of each cDNA preparation was amplified by PCR using oligonucleotide primers sense 5'(ATG TCT GCA AGC ACC ATG GCT AAG)3', representing amino acids −30 to −23 and antisense 5'(CTG AGA TTT AGC CTT AAC TAA TAC)3' representing amino acids 77 to 84 of rat pre-pro PTH mRNA. PCR conditions were denaturation 94 C×1 min., annealing 60 C×1 min. and extension 72 C×2 min. for 18 cycles. Amplification of β-actin mRNA from the cDNA was achieved using the same conditions with primers sense 5'(GAT GAT ATC GCC GCG CTC GTC GTC GAC)3' and antisense 5'(AGC CAG GTC CAG ACG CAG GAT GGC ATG)3' with a total of 26 cycles. PCR products were separated by means of 1.2% agarose gels in TAE buffer containing ethidium bromide. The gels were photographed on an ultraviolet light box with Polaroid type 665 film to yield a negative. The Polaroid negative of each gel was scanned (Omni Media 6cx/csx, X-ray Scanner Corporation, Torrance, Calif.) and analyzed using Sepra Scan 2001 software (Integrated Separation Systems, Natwick, Mass.). The amount of pre-pro PTH and β-actin mRNA from up to 32 different animals could be processed simultaneously to eliminate potential interassay variation. Sequencing of plasmids (pCRII, Invitrogen) containing the PCR products established their identity as rat pre-pro PTH and rat β-actin.

Calcemic Response to 1,25-(OH)$_2$D$_3$ and 19-nor-1,25-(OH)$_2$D$_2$

Renal insufficiency was induced in a group of 150 female Sprague-Dawley rats by 5/6 nephrectomy. The procedure entails the ligation of most of the branches of the left renal artery and right nephrectomy. The rats were fed a diet containing 0.6% calcium and 0.7% phosphorus for a period of eight weeks. At the end of this period, all the rats weighed approximately the same amount (range 260 to 280 gm).

To determine the response to 1,25-(OH)$_2$D$_3$ or 19-nor-1, 25-(OH)$_2$D$_2$ on serum calcium, uremic rats were injected intraperitoneally (IP) on a daily basis for a period of 10 days with vehicle (propylene glycol 100 μl), 1,25-(OH)$_2$D$_3$, 10 ng/rat, or 19-nor-1,25-(OH)$_2$D$_2$ (10, 100, or 1,000 ng/rat).

To determine the response of the parathyroid glands to 1,25-(OH)$_2$D$_3$ or 19-nor-1,25-(OH)$_2$D$_2$, rats with chronic renal insufficiency were divided into three main groups: 1) Vehicle; 2) 1,25-(OH)$_2$D$_3$ (2.0, 4.0, or 8.0 ng/rat), and 3) 19-nor-1,25-(OH)$_2$D$_2$ (8.0, 25, or 75 ng/rat) given IP every other day for a period of eight days. In addition, studies were performed in normal animals.

Analytical Determinations

Total calcium was determined by atomic absorption spectrophotometry (Perkin Elmer, Model 1100B, Norwalk, Conn.), and ICa by an ionized-calcium-specific electrode (Model ICA-1, Radiometer, Copenhagen). Plasma phosphorus and creatinine were determined by autoanalyzer (COBAS MIRA Plus, Branchburg, N.J.). Intact PTH was measured by an IRMA specific for intact rat PTH from Nichols Institute (San Capistrano, Calif.). The diet was purchased from DYETS, Inc. (Bethlehem, Pa.). 1,25-(OH)$_2$D$_3$ was provided by Dr. Milan Uskokovic (Hoffman La Roche Laboratories, Nutley, N.J., USA), and 19-nor-1, 25-(OH)$_2$D$_2$ was provided by Abbott Laboratories, Abbott Park, Ill., USA.

Statistical Analysis

All data are expressed as mean ±SEM. One-way analysis of variance (ANOVA) was used for comparisons between groups.

RESULTS

Formula 1 where $X^1$ and $X^2$ are both hydrogen and R is side chain (c) illustrates the chemical structure of 19-nor-1, 25-(OH)$_2$D$_2$. This analog has the carbon 28 and the double bond at carbon 22 that are characteristic of vitamin D$_2$ compounds, but it lacks carbon 19 and the exocyclic double bond found in all natural vitamin D metabolites.

The effect of 1,25-$(OH)_2D_3$ and 19-nor-1,25-$(OH)_2D_2$ on PTH secretion in primary culture of bovine parathyroid cells are described in FIG. 1. All groups had PTH secretion measured at the same time on the final day in culture (72 hours). Both compounds have a significant dose-dependent suppressive effect on PTH secretion ($p<0.001$). The maximum suppressive effect was obtained with both compounds at a concentration of $10^{-7}$M. There was no significant difference in the suppressive effect on PTH secretion in vitro between the two compounds.

Figure 2:
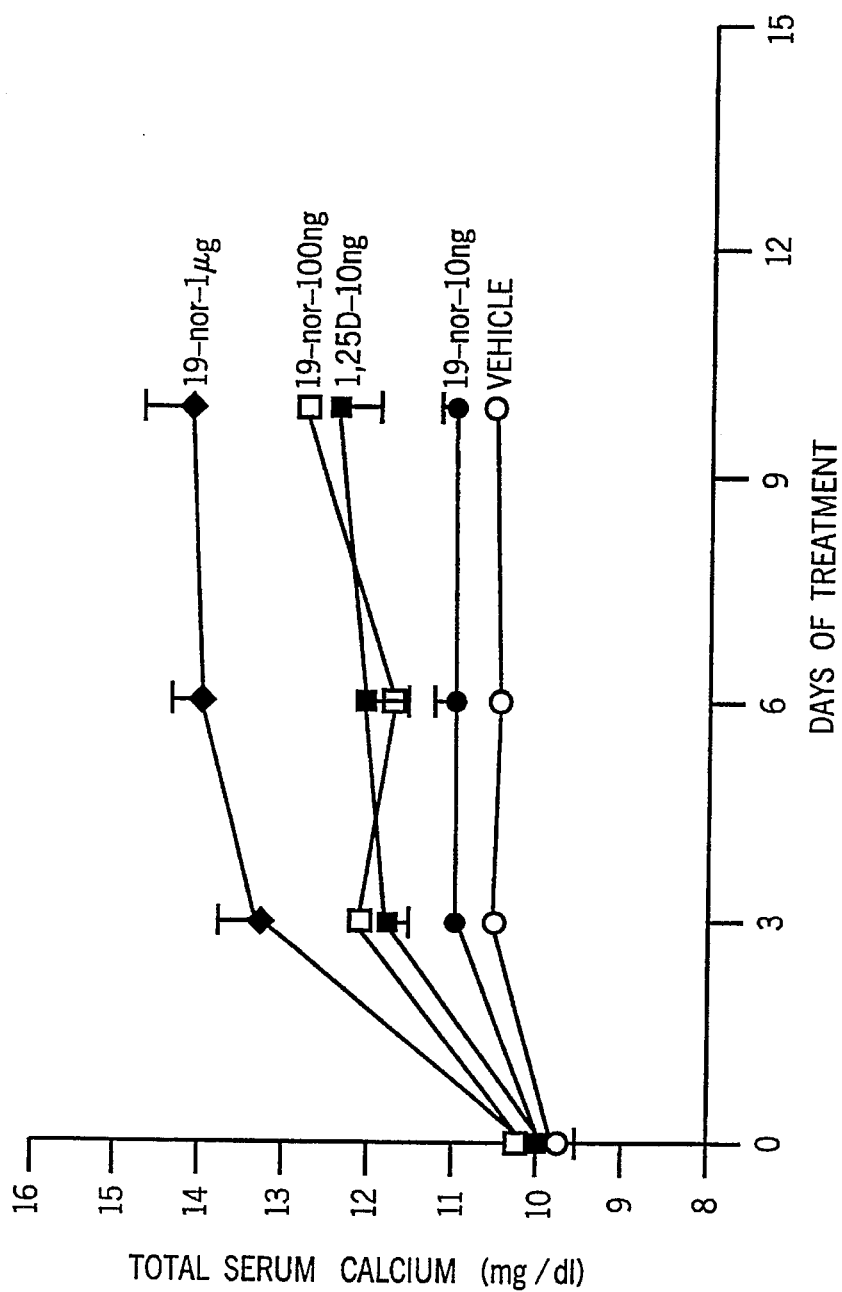
FIG. 2 illustrates the comparative effects of 1,25-$(OH)_2D_3$ and 19-nor-1,25-$(OH)_2D_2$ on serum calcium in uremic rats.

Comparative effects of 1,25-$(OH)_2D_3$ and 19-nor-1,25-$(OH)_2D_2$ on total serum calcium are shown in FIG. 2. The rats were injected IP on a daily basis for a period of 10 days with vehicle (propylene glycol 100 µl), 1,25-$(OH)_2D_3$ (10 ng/rat), or 19-nor1,25-$(OH)_2D_2$ (10, 100 or 1,000 ng/rat). Daily injections (IP) or 19-nor-1,25-$(OH)_2D_2$ (10 ng/rat) did not significantly increase serum calcium. When the dose of 19-nor-1,25-$(OH)_2D_2$ was increased to 100 ng/rat, the increment on serum calcium was the same as that induced by 1,25-$(OH)_2D_3$ at 10 ng/rat. All the biochemical parameters measured at the time of sacrifice (two months of renal insufficiency) are depicted in Table 1 and FIGS. 3 and 4. Serum creatinine increased from 0.64±0.02 in the normal rats to 1.15±0.05 mg/dl in uremic animals ($p<0.001$). Neither 1,25-$(OH)_2D_3$ nor 19-nor-1,25-$(OH)_2D_2$ modified the serum creatinine in the uremic animals.

Figure 3:
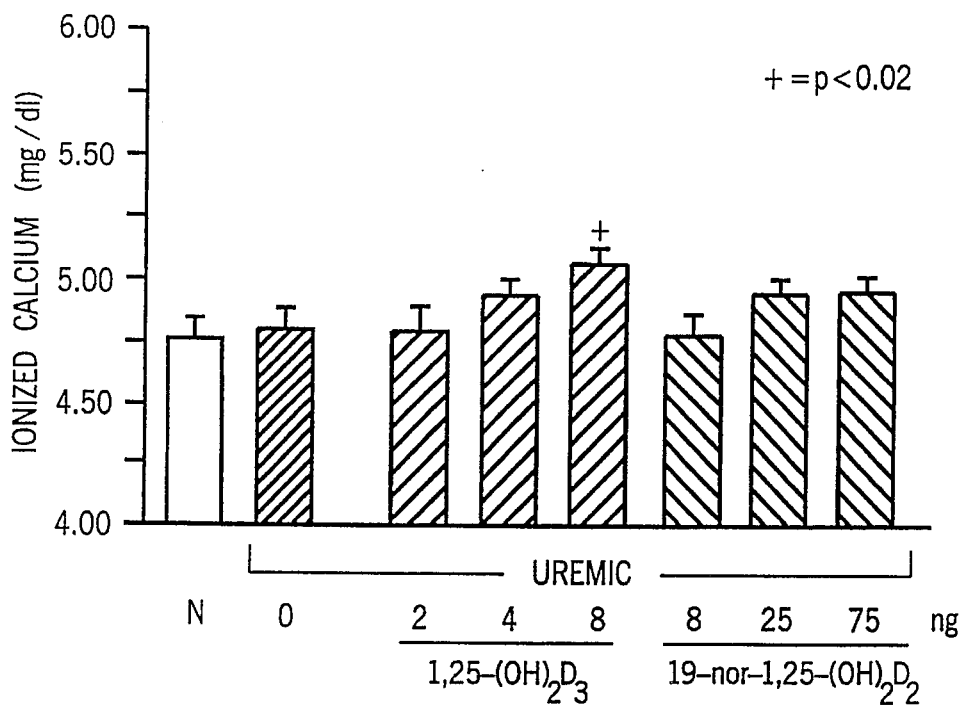
FIG. 3 illustrates the comparative effects of 1,25-$(OH)_2D_3$ and 19-nor-1,25-$(OH)_2D_2$ on ionized calcium in uremic rats.

As shown in FIG. 3, serum ionized calcium increased in the uremic rats receiving 8 ng 1,25-$(OH)_2D_3$ every other day for eight days (5.08±0.06 vs. 4.81±08 mg/dl in the uremic control animals, $p<0.02$,). 19-nor-1,25-$(OH)_2D_2$ did not increase serum ionized calcium even at the larger dose (75 ng/rat×4 times).

Figure 4:
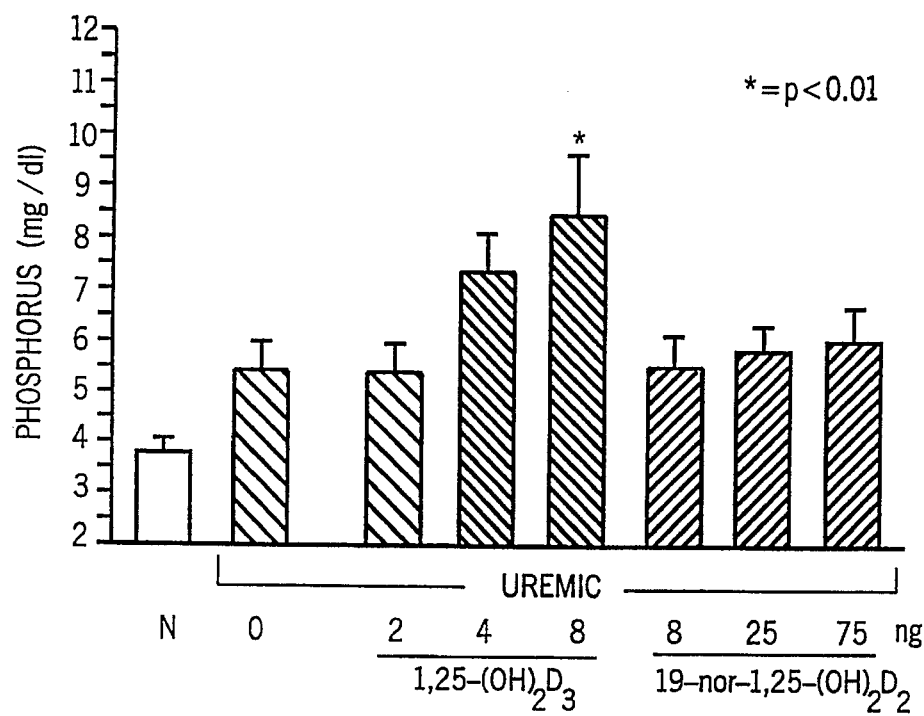
FIG. 4 illustrates the comparative effects of 1,25-$(OH)_2D_3$ and 19-nor-1,25-$(OH)_2D_2$ on serum phosphorus.
Figure 5:
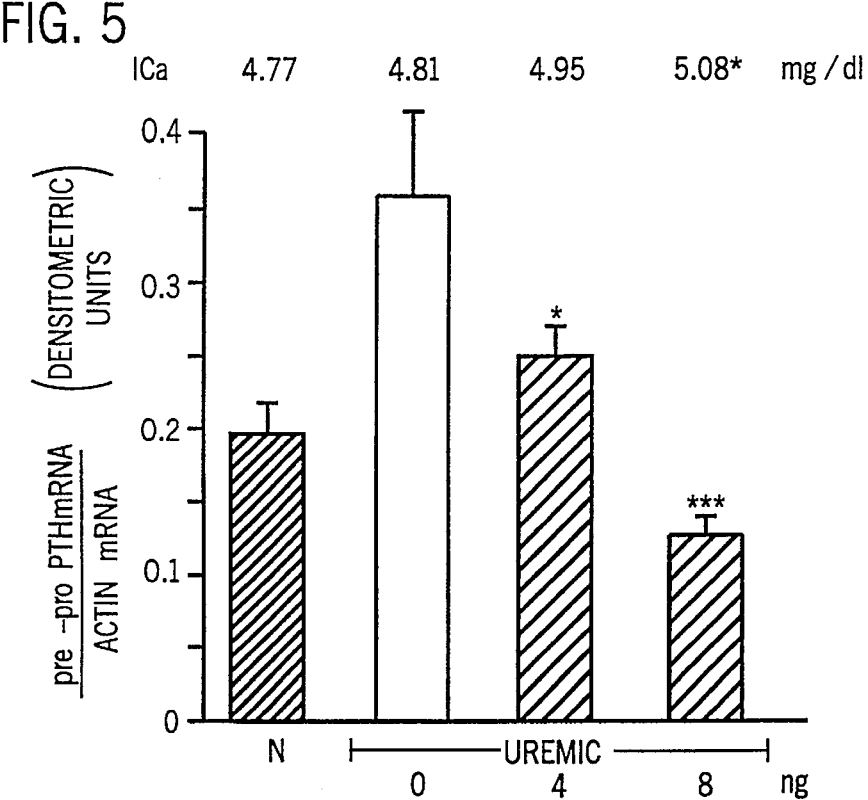
FIG. 5 illustrates the effects of 1,25-$(OH)_2D_3$ on pre-pro PTH mRNA.
Figure 6:
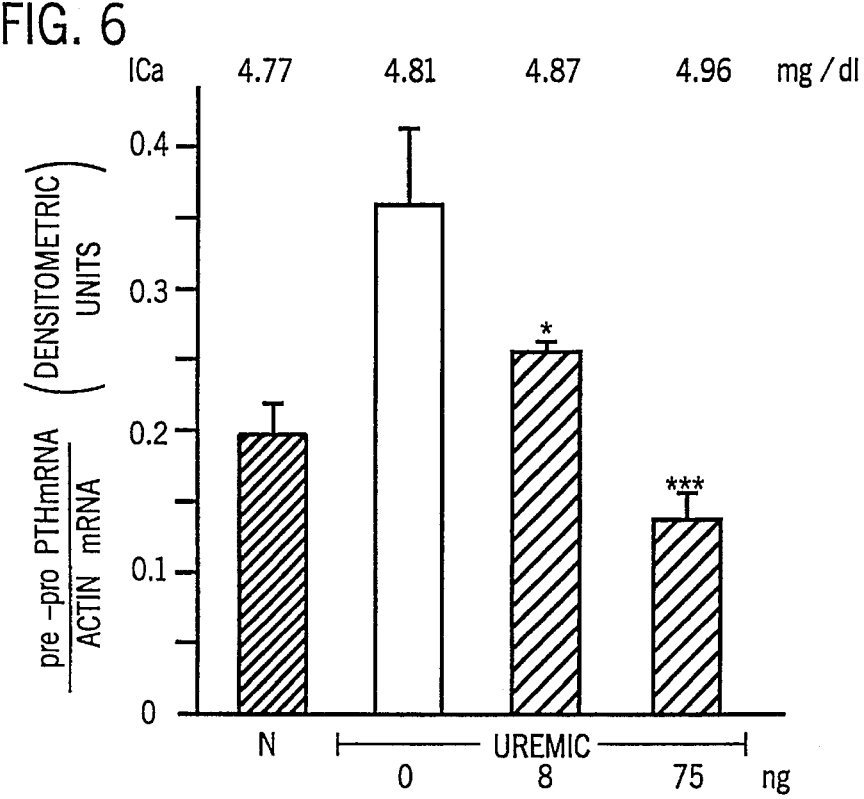
FIG. 6 illustrates the effects of 19-nor-1,25-$(OH)_2D_2$ on pre-pro PTH mRNA.

As shown in FIG. 4, 1,25-$(OH)_2D_3$ (8 ng dose) increased serum phosphorus from 5.57±0.5 (uremic control) to 8.64±1.15 mg/dl ($p<0.01$). None of the doses of 19-nor-1,25$(OH)_2D_2$ increased serum phosphorus (Table I, FIG. 4). Parathyroid hormone in the normal rats was 40±8.6 pg/ml and increased to 243±83 pg/ml in the uremic rats. The only dose of 1,25-$(OH)_2D_3$ that produced a statistically significant ($p<0.01$) decrease in levels of PTH was the 8 ng dose. PTH decreased from 202±31 to 90±20 pg/ml. (However, ICa increased from 4.81±0.08 to 5.08+0.06 mg/dl ($p<0.02$) (FIG. 5).) All the doses of 19-nor-1,25-$(OH)_2D_2$ (8, 25, 75) produced a significant decrease in the levels of circulating PTH. The greater effect was observed with the 75 ng dose. PTH decreased from 225±60 to 53±16 pg/ml (FIG. 6) (7.5% decrease); however, none of the doses of 19-nor-1,25-$(OH)_2D_2$ increased ionized calcium.

Figure 7:
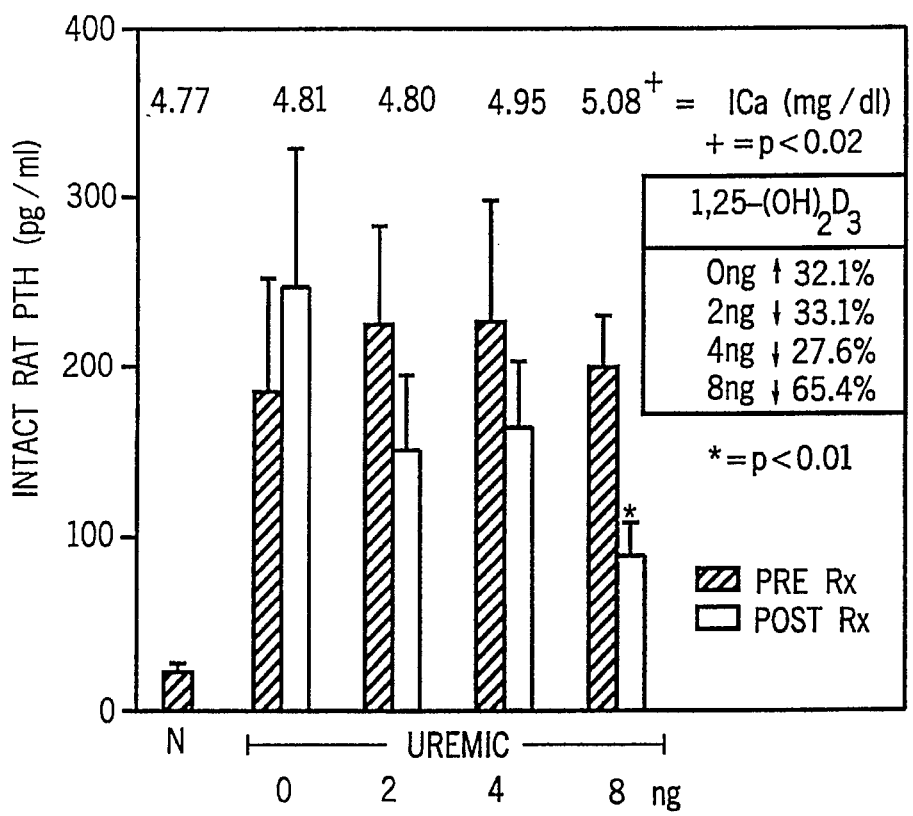
FIG. 7 illustrates the effects of 1,25-$(OH)_2D_3$ on serum PTH.
Figure 8:
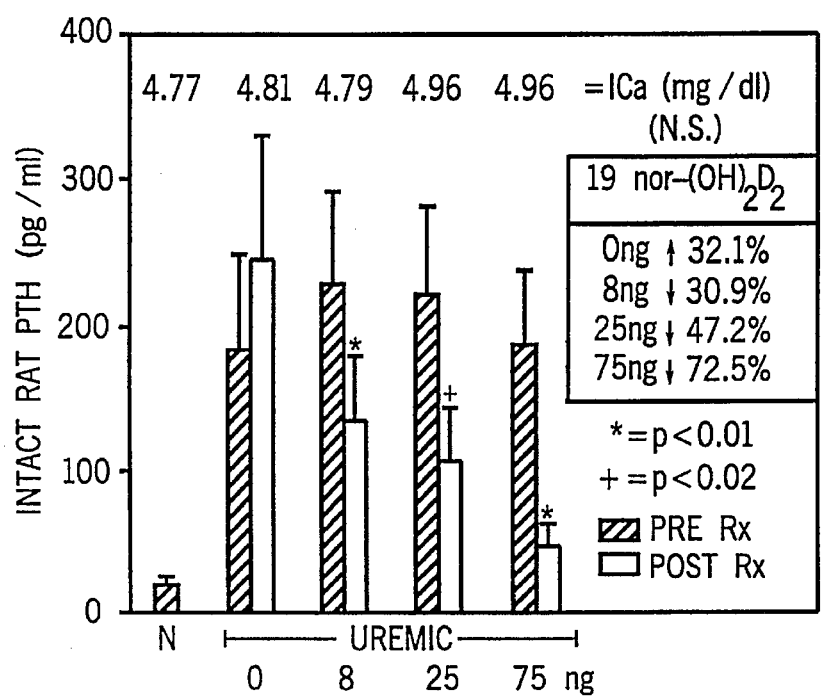
FIG. 8 illustrates the effects of 19-nor-1,25-$(OH)_2D_2$ on serum PTH.

The results of reverse transcriptase (PCR on pre-pro PTH mRNA are depicted in FIGS. 7 and 8, 1,25-$(OH)_2D_3$ suppressed pre-pro PTH mRNA in a dose-dependent manner (FIG. 7). Similar results were obtained with 19-nor-1,25-$(OH)_2D_2$ (FIG. 8).

DISCUSSION

Chronic renal insufficiency is characterized by changes in mineral homeostasis, with secondary. hyperparathyroidism appearing even in the early stages of renal insufficiency leading to the development of renal osteodystrophy. Both low levels of 1,25-$(OH)_2D_3$ and phosphate retention are responsible for the development of secondary hyperparathyroidism. Although serum phosphorus is usually normal in patients with early renal insufficiency, phosphate restriction can reduce secondary hyperparathyroidism. Dietary phosphate restriction increases 1,25-$(OH)_2D_3$ levels, Portale et al, "Effect of Dietary Phosphorus on Circulating Concentrations of 1,25-dihydroxyvitamin D and Immunoreactive Parathyroid Hormone in Children with Moderate Renal Insufficiency", J. Clin. Invest. 73:1580–1589, 1984, which in turn decreases PTH by directly suppressing PTH gene transcription and by increasing intestinal calcium absorption. In later stages of renal failure, the extent of hyperparathyroidism and 1,25-$(OH)_2D_3$ deficiency increases, and phosphate restriction has little effect on 1,25-$(OH)_2D_3$ levels, Lopez-Hilker et al, "Phosphorus Restriction Reverses Hyperparathyroidism in Uremia Independent of Changes in Calcium and Calcitriol", Am. J. Physiol. 259:F432–F437, 1990, presumably, due to the decreased renal mass available for 1,25-$(OH)_2D_3$ synthesis.

Several vitamin D analogs with low calcemic activity have been found to be nearly as effective as 1,25-$(OH)_2D_3$ in suppressing PTH secretion by cultured bovine parathyroid cells. This includes 22-oxacalcitriol (OCT), Brown et al, "The Non-Calcemic Analog of Vitamin D, 22-oxacalcitriol (OCT) Suppresses Parathyroid Hormone Synthesis and Secretion", J. Clin. Invest. 84:728–732, 1989, as well as 1,25-$(OH)_2$-16-ene-23-yne-$D_3$, 1,25-$(OH)_2$-24-dihomo-$D_3$, and 1,25-$(OH)_2$-24-trihomo-22-ene-$D_3$ (unpublished data). To date, only 22-oxacalcitriol has been examined in detail for this action in vivo. Brown and collaborators, Brown et al, "Selective Vitamin D Analogs and their Therapeutic Applications", Sem. Nephrol 14:156–174, 1994, reported that 22-oxacalcitriol, despite its rapid clearance in vivo, could suppress PTH mRNA. Low, submaximal doses of calcitriol and OCT produced comparable inhibition. OCT has also been shown to suppress serum PTH in uremic rats and dogs. In the current study, we used an analog of 1.25-$(OH)_2D_3$ with low calcemic and phosphatemic action, 19-nor-1.25-$(OH)_2D_2$. This analog of calcitriol has the carbon 28 and the double bond at carbon 22 that are characteristic of vitamin $D_2$ compounds, but it lacks carbon 19 and the exocyclic double bond found in all natural vitamin D compounds. We first performed studies in vitro, utilizing a primary culture of bovine parathyroid cells. 19-nor-1,25-$(OH)_2D_2$ had a similar suppressive effect on PTH as 1,25-$(OH)_2D_3$. A 52% suppression on PTH release was obtained with 19-nor-1,25-$(OH)_2D_2$, $10^{-7}$M. There was no significant difference in the suppressive effect of PTH secretion between the two compounds. Thereafter, preliminary studies were performed in vivo to determine the calcemic activity of 19-nor-1,25-$(OH)_2D_2$. It was found that 1,25-$(OH)_2D_3$ (10 ng/rat/10 days) increased serum calcium to the same magnitude as 19-nor-1,25-$(OH)_2D_2$ (100 ng/rat/10 days). Because of this, three different doses of 1,25-$(OH)_2D_3$ (2, 4, and 8 ng) and 19-nor- 1,25-$(OH)_2D_2$ (8, 25, and 75 ng) were selected for the chronic studies. After two months of renal insufficiency, the animals received the above two compounds at the three indicated doses four times during a period of eight days. As expected, 1,25-$(OH)_2D_3$ suppressed pre-pro PTH mRNA and PTH secretion. However, this decrease was statistically significant only with the 8 ng dose. This dose induced hypercalcemia and hyperphosphatemia. On the other hand, none of the doses of 19-nor-1,25-$(OH)_2D_2$ produced statistically significant changes in serum ionized calcium or serum phosphorus. However, all doses of 19-nor-1,25-$(OH)_2D_2$ were effective in suppressing both pre-pro PTH mRNA and PTH secretion. Since a radioactive form of 19-nor-1,25-$(OH)_2D_2$ was not available during these studies, we were unable to determine protein binding and a half-life of the analog. However previous studies by DeLuca indicate that 19-nor-1,25-$(OH)_2D_2$ binds approximately ⅓ as well as 1,25-$(OH)_2D_3$ to the porcine intestinal vitamin D receptor when compared to 1,25-$(OH)_2D_3$ (unpublished results).

From the clinical point of view, one of the most difficult biochemical alterations to correct in hemodialysis patients is hyperphosphatemia. Patients on dialysis usually ingest approximately 1.0 to 1.4 grams of phosphorus per day. Since the maximum amount of phosphorus that is removed during each dialysis approximates 800 to 1,000 mg, Hou et al, "Calcium and Phosphorus Fluxes During Hemodialysis with Low Calcium Dialysate", Am. J. Kidney Dis. 18:217–224, 1991, the remaining 2.5 to 3.5 grams of phosphorus ingested per week must be removed by other means. Thus, the use of phosphate binders such as calcium carbonate and calcium acetate are usually utilized to correct the hyperphosphatemia, Emmett et al, "Calcium Acetate Control of Serum Phosphorus in Hemodialysis Patients", Am. J. Kidney Dis. 27:544–550, 1991; Schaefer et al, "The Treatment of Uraemic Hyperphosphataemia with Calcium Acetate and Calcium Carbonate: A Comparative Study", Nephrol Dial Transplant 6:170–175, 1991; Delmez et al, "Calcium Acetate as a Phosphorus Binder in Hemodialysis Patients", J. Am. Soc. Nephrol 3:96–102, 1992. Unfortunately, 1,25-$(OH)_2D_3$ not only increases the absorption of calcium, but also of phosphorus, making hyperphosphatemia more difficult to be treated. Thus, the hyperphosphatemia induced in part by the action of 1,25-$(OH)_2D_3$ requires a further addition of calcium carbonate or calcium acetate, which can greatly increase the levels of serum ionized calcium. The high calcium-phosphate product that the patient may develop imposes a tremendous risk for the development of metastatic calcifications, Arora et al, "Calcific Cardiomyopathy in Advanced Renal Failure", Arch. Intern. Med. 1335:603–605 1975; Rostand et al, "Myocardial Calcification and Cardiac Dysfunction in Chronic Renal Failure", Am. J. Med. 85: 651–657, 1988; Gipstein et al, "Calciphylaxis in Man A Syndrome of Tissue Necrosis and Vascular Calcifications in 11 Patients with Chronic Renal Failure", Arch. Intern. Med. 136:1273–1280, 176; Milliner et al, "Soft Tissue Calcification in Pediatric Patients with End-stage Renal Disease", Kidney Int. 38:931–936, 1990. Therefore, the treatment demands a decrease in the amount of 1,25-$(OH)_2D_3$ administered to the patient thus decreasing the effectiveness of 1,25-$(OH)_2D_3$ therapy for controlling PTH secretion.

The development of an analog of 1,25-$(OH)_2D_3$ with minimal effect on calcium and phosphorus, such as 19-nor-$_{1,25}$-$(OH)_2D_2$, is an ideal tool for the treatment of secondary hyperparathyroidism and renal osteodystrophy. This analog (19-nor-1,25-$(OH)_2D_2$) has been shown to be as effective as 1,25-$(OH)_2D_3$ in suppressing PTH in vitro and in rats with chronic renal insufficiency. In addition, the effects on calcium and phosphorus are minimal, allowing the use of larger doses of this compound to suppress secondary hyperparathyroidism. Although no studies have been performed in humans up to this point, the fact that all three doses of 19-nor-1,25-$(OH)_2D_2$ were effective in suppressing PTH secretion indicates a large therapeutic window for this compound.

In summary, we have demonstrated that 19-nor-$_{1,25}$-$(OH)_2D_2$, a new analog of calcitriol with a low calcemic and phosphatemic effect, is effective in suppressing parathyroid hormone in uremic rats with secondary hyperparathyroidism.

TABLE 1

| | | | BLOOD CHEMISTRIES[a] | | | | | |
| --- | --- | --- | --- | --- | --- | --- | --- | --- |
| | | | Uremic + 1,25-$(OH)_2D_3$ | | | Uremic + 19-nor-1,25-$(OH)_2D_3$ | | |
| | Normal n = 8 | Uremic n = 11 | 2 ng n = 13 | 4 ng n = 11 | 8 ng n = 13 | 8 ng n = 14 | 25 ng n = 12 | 75 ng n = 12 |
| Serum Creatinine mg/dl | 0.64 ± .02* | 1.15 ± .05 | 1.18 ± .06 | 1.12 ± .04 | 1.15 ± .07 | 1.20 ± .06 | 1.18 ± .05 | 1.16 ± .16 |
| ICa mg/dl | 4.77 ± .07 | 4.81 ± .08 | 4.80 ± .10 | 4.95 ± .06 | 5.08 ± .06‡ | 4.79 ± .09 | 4.96 ± .05 | 4.96 ± .06 |
| Phosphorus mg/dl | 3.76 ± .27 | 5.57 ± .50 | 5.47 ± .52 | 7.45 ± .80 | 8.64 ± 1.15* | 5.68 ± .57 | 5.98 ± .49 | 6.17 ± .68 |
| PTH pg/ml | 40 ± 8.6 | 247 ± 83 | 152 ± 45 | 166 ± 40 | 90 ± 20* | 137 ± 47* | 111 ± 38‡ | 53 ± 16* |

[a]All data are mean ± SEM, n = 11–14 per group.
*P < 0.01 vs. uremic control.
‡P < 0.02 vs. uremic control.

We claim:

1. A method of treating a patient having renal osteodystrophy while avoiding hyperphosphatemia comprising administering to said patient a vitamin D compound that has minimal effect on blood serum phosphorus of said patient, said vitamin D compound selected from a 19-nor-vitamin $D_2$ compound having the formula:

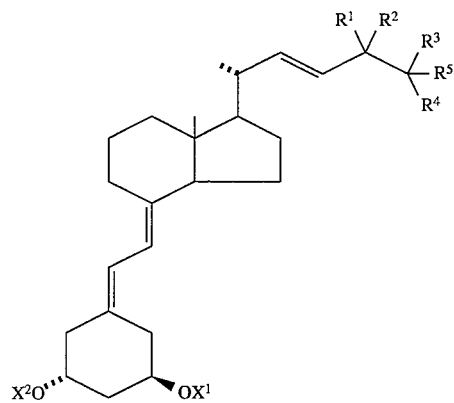

where $X^1$ and $X^2$ each represent, independently, hydrogen or a hydroxy-protecting group; and where $R^1$ is selected from hydrogen, hydroxy, protected hydroxy, fluoro, trifluoromethyl, and $C_{1-5}$— alkyl, which may be straight chain or branched and, optionally, bear a hydroxy or protected-hydroxy substituent; and where each of $R^2$, $R^3$, and R4, independently, is selected from hydrogen, fluoro, trifluoromethyl and $C_{1-5}$ alkyl, which may be straight-chain or branched, and optionally, bear a hydroxy or protected-hydroxy substituent; and where $R^1$ and $R^2$, taken together represent an oxo group, or an alkylidene group, $=CR^2R^3$, or the group $-(CH_2)_p-$, where p is an integer from 2 to 5; and where $R^3$ and $R^4$, taken together, present an oxo group, or a group $-(CH_2)_q-$, where q is an integer from 2 to 5; and where $R^5$ represents hydrogen, hydroxy, protected hydroxy, or $C_{1-5}$ alkyl.

2. The method of claim 1 wherein said vitamin D compound is administered together with a pharmaceutically accept, able excipient.

3. The method of claim 1 wherein said vitamin D compound is in a solid or liquid vehicle ingestible by and non-toxic to the patient.

4. The method of claim 1 where the said vitamin D compound is 1α,25-dihydroxy-19-nor-vitamin $D_2$.

5. The method of claim 1 where the said vitamin D compound is 1α-hydroxy-19-nor-vitamin $D_2$.

6. The method of claim 1 where the said vitamin D compound is 1α-hydroxy-19-nor-24-epi-vitamin $D_2$.

7. The method of claim 1 where the said vitamin D compound is 1α,25-dihydroxy),-19-nor-24-epi-vitamin $D_2$.

8. The method of claim 1 where the said vitamin D compound is administered orally.

9. The method of claim 1 where the said vitamin D compound is administered parenterally.

10. The method of claim 1 where the said vitamin D compound is administered topically.

11. The method of claim 1 where the said vitamin D compound is administered in an amount from 1 µg to about 500 µg per day to the patient.

* * * * *

UNITED STATES PATENT AND TRADEMARK OFFICE
CERTIFICATE OF CORRECTION

PATENT NO. : 5,597,815
DATED : January 28, 1997
INVENTOR(S) : Hector F. DeLuca et al It is certified that error appears in the above-indentified patent and that said Letters Patent is hereby corrected as shown below:

| | |
|---|---|
| Claim 1, line 66 | Delete "R4" and substitute therefor ---$R^4$--- |
| Claim 2, line 12 | Delete "accept, able" and substitute therefor ---acceptable--- |
| Claim 7, line 2 | After "dihydroxy" delete ")," |

Signed and Sealed this

First Day of July, 1997

*Attest:*

BRUCE LEHMAN

*Attesting Officer*     *Commissioner of Patents and Trademarks*